US012042246B2

(12) United States Patent
Bar-Tal et al.

(10) Patent No.: US 12,042,246 B2
(45) Date of Patent: *Jul. 23, 2024

(54) MULTI-FUNCTION CONDUCTING ELEMENTS FOR A CATHETER

(71) Applicant: Biosense Webster (Israel) Ltd., Yokneam (IL)

(72) Inventors: Meir Bar-Tal, Haifa (IL); Michael Levin, Haifa (IL); Avi Reuveni, Givat Shmuel (IL); Debby Esther Highsmith, Laguna Niguel, CA (US); Ariel Garcia, Glendora, CA (US); Daniel Osadchy, Irvine, CA (US); Shmuel Auerbach, Kerem Maharal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 265 days.

This patent is subject to a terminal disclaimer.

(21) Appl. No.: 17/163,096

(22) Filed: Jan. 29, 2021

(65) Prior Publication Data
US 2021/0145282 A1    May 20, 2021

Related U.S. Application Data

(63) Continuation of application No. 15/359,838, filed on Nov. 23, 2016, now Pat. No. 10,905,329, which is a
(Continued)

(51) Int. Cl.
*A61B 18/18* (2006.01)
*A61B 5/00* (2006.01)
(Continued)

(52) U.S. Cl.
CPC ............ *A61B 5/0036* (2018.08); *A61B 5/062* (2013.01); *A61B 5/287* (2021.01); *A61B 5/4836* (2013.01);
(Continued)

(58) Field of Classification Search
CPC ..... A61B 5/4836; A61B 34/20; A61B 5/0422; A61B 5/062; A61B 5/6853; A61B 5/6858;
(Continued)

(56) References Cited

U.S. PATENT DOCUMENTS

D123,782 S    12/1940 Paul
3,316,896 A    5/1967 Louis
(Continued)

FOREIGN PATENT DOCUMENTS

CN    101088459 A    12/2007
CN    101384214 A    3/2009
(Continued)

OTHER PUBLICATIONS

Extended European Search Reporte dated Nov. 12, 2020, from corresponding EP Appl. No. 20190495.0.
(Continued)

*Primary Examiner* — Joseph A Stoklosa
*Assistant Examiner* — Brian M Antiskay
(74) *Attorney, Agent, or Firm* — Troutman Pepper Hamilton Sanders LLP (57) ABSTRACT

Described embodiments include an apparatus that includes an expandable structure, configured for insertion into a body of a subject, and a plurality of conducting elements coupled to the expandable structure. Each of the conducting elements comprises a respective coil and has an insulated portion that is electrically insulated from tissue of the subject, and an uninsulated portion configured to exchange signals with the tissue, while in contact with the tissue. Other embodiments are also described.

15 Claims, 3 Drawing Sheets

Related U.S. Application Data continuation-in-part of application No. 15/177,775, filed on Jun. 9, 2016, now Pat. No. 10,905,329.

(51) Int. Cl.
*A61B 5/06* (2006.01)
*A61B 5/287* (2021.01)
*A61B 18/00* (2006.01)
*A61B 18/14* (2006.01)
*A61B 34/20* (2016.01)

(52) U.S. Cl.
CPC .......... *A61B 5/6853* (2013.01); *A61B 5/6858* (2013.01); *A61B 5/7445* (2013.01); *A61B 18/1492* (2013.01); *A61B 34/20* (2016.02); *A61B 5/4848* (2013.01); *A61B 2018/0022* (2013.01); *A61B 2018/00267* (2013.01); *A61B 2018/00351* (2013.01); *A61B 2018/00577* (2013.01); *A61B 2018/00821* (2013.01); *A61B 2018/00875* (2013.01); *A61B 2034/2053* (2016.02)

(58) Field of Classification Search
CPC .............. A61B 5/7445; A61B 18/1492; A61B 2034/2053; A61B 5/4848; A61B 2018/0022; A61B 2018/00267; A61B 2018/00351; A61B 2018/100577; A61B 2018/00821; A61B 2018/00875
USPC ........ 600/372–374, 377, 381, 407, 422–424, 600/434–435, 508–509; 606/14
See application file for complete search history.

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,699,147 A | 10/1987 | Chilson et al. |
| 4,709,698 A | 12/1987 | Johnston et al. |
| 4,805,621 A | 2/1989 | Heinze et al. |
| 4,940,064 A | 7/1990 | Desai |
| 5,178,957 A | 1/1993 | Kolpe et al. |
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,429,617 A | 7/1995 | Hammersmark et al. |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,505,730 A | 4/1996 | Edwards |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,582,609 A | 12/1996 | Swanson et al. |
| 5,584,830 A | 12/1996 | Ladd et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,702,386 A | 12/1997 | Stern et al. |
| 5,718,241 A | 2/1998 | Ben-Haim et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,797,903 A | 8/1998 | Swanson et al. |
| 5,823,189 A | 10/1998 | Kordis |
| 5,860,974 A | 1/1999 | Abele |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 5,971,983 A | 10/1999 | Lesh |
| 6,012,457 A | 1/2000 | Lesh |
| 6,014,579 A | 1/2000 | Pomeranz et al. |
| 6,014,590 A | 1/2000 | Whayne et al. |
| 6,024,740 A | 2/2000 | Lesh et al. |
| 6,042,580 A | 3/2000 | Simpson |
| 6,050,267 A | 4/2000 | Nardella et al. |
| 6,070,094 A | 5/2000 | Swanson et al. |
| 6,119,030 A | 9/2000 | Morency |
| 6,123,718 A | 9/2000 | Tu et al. |
| 6,142,993 A | 11/2000 | Whayne et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,216,043 B1 | 4/2001 | Swanson et al. |
| 6,216,044 B1 | 4/2001 | Kordis |
| 6,226,542 B1 | 5/2001 | Reisfeld |
| 6,233,491 B1 | 5/2001 | Kordis et al. |
| 6,272,371 B1 | 8/2001 | Shlomo |
| 6,301,496 B1 | 10/2001 | Reisfeld |
| 6,322,558 B1 | 11/2001 | Taylor et al. |
| 6,332,880 B1 | 12/2001 | Yang et al. |
| 6,380,957 B1 | 4/2002 | Banning |
| 6,402,740 B1 | 6/2002 | Ellis et al. |
| 6,428,537 B1 | 8/2002 | Swanson et al. |
| D462,389 S | 9/2002 | Provence et al. |
| 6,456,864 B1 | 9/2002 | Swanson et al. |
| 6,471,693 B1 | 10/2002 | Carroll et al. |
| 6,511,478 B1 | 1/2003 | Burnside et al. |
| 6,522,930 B1 | 2/2003 | Schaer et al. |
| 6,569,160 B1 | 5/2003 | Goldin et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,656,174 B1 | 12/2003 | Hegde et al. |
| 6,735,465 B2 | 5/2004 | Panescu |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,785,571 B2 | 8/2004 | Glossop |
| 6,814,733 B2 | 11/2004 | Schwartz et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,893,433 B2 | 5/2005 | Lentz |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 6,986,744 B1 | 1/2006 | Krivitski |
| 6,987,995 B2 | 1/2006 | Drysen |
| 6,997,924 B2 | 2/2006 | Schwartz et al. |
| 7,048,734 B1 | 5/2006 | Fleischman et al. |
| 7,142,903 B2 | 11/2006 | Rodriguez et al. |
| 7,149,563 B2 | 12/2006 | Fuimaono et al. |
| 7,156,816 B2 | 1/2007 | Schwartz et al. |
| 7,255,695 B2 | 8/2007 | Falwell et al. |
| 7,257,434 B2 | 8/2007 | Fuimaono et al. |
| 7,274,957 B2 | 9/2007 | Drysen |
| 7,340,307 B2 | 3/2008 | Maguire et al. |
| 7,377,906 B2 | 5/2008 | Selkee |
| 7,399,299 B2 | 7/2008 | Daniel et al. |

(56) References Cited

U.S. PATENT DOCUMENTS

| | | |
|---|---|---|
| 7,410,486 B2 | 8/2008 | Fuimaono et al. |
| 7,442,190 B2 | 10/2008 | Abboud et al. |
| 7,522,950 B2 | 4/2009 | Fuimaono et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,697,972 B2 | 4/2010 | Verard et al. |
| RE41,334 E | 5/2010 | Beatty et al. |
| 7,720,517 B2 | 5/2010 | Drysen |
| 7,756,576 B2 | 7/2010 | Levin |
| 7,842,031 B2 | 11/2010 | Abboud et al. |
| 7,846,157 B2 | 12/2010 | Kozel |
| 7,853,302 B2 | 12/2010 | Rodriguez et al. |
| 7,930,018 B2 | 4/2011 | Harlev et al. |
| 8,000,765 B2 | 8/2011 | Rodriguez et al. |
| 8,007,495 B2 | 8/2011 | McDaniel et al. |
| 8,021,327 B2 | 9/2011 | Selkee |
| 8,048,032 B2 | 11/2011 | Root et al. |
| 8,048,063 B2 | 11/2011 | Aeby et al. |
| 8,097,926 B2 | 1/2012 | De Graff et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,231,617 B2 | 7/2012 | Satake |
| 8,235,988 B2 | 8/2012 | Davis et al. |
| 8,267,932 B2 | 9/2012 | Baxter et al. |
| 8,275,440 B2 | 9/2012 | Rodriguez et al. |
| 8,346,339 B2 | 1/2013 | Kordis et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| D690,318 S | 9/2013 | Kluttz et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| D694,652 S | 12/2013 | Tompkin |
| 8,641,709 B2 | 2/2014 | Sauvageau et al. |
| 8,712,550 B2 | 4/2014 | Grunewald |
| 8,721,590 B2 | 5/2014 | Seward et al. |
| 8,755,861 B2 | 6/2014 | Harlev et al. |
| 8,777,161 B2 | 7/2014 | Pollock et al. |
| 8,825,130 B2 | 9/2014 | Just et al. |
| D716,340 S | 10/2014 | Bresin et al. |
| 8,852,181 B2 | 10/2014 | Malecki et al. |
| 8,906,011 B2 | 12/2014 | Gelbart et al. |
| 8,918,184 B1 | 12/2014 | Torgerson et al. |
| D720,766 S | 1/2015 | Mandal et al. |
| D721,379 S | 1/2015 | Moon et al. |
| 8,945,120 B2 | 2/2015 | McDaniel et al. |
| D724,618 S | 3/2015 | Shin |
| 8,979,839 B2 | 3/2015 | De La Rama et al. |
| 8,998,893 B2 | 4/2015 | Avitall |
| D729,263 S | 5/2015 | Ahn et al. |
| 9,037,264 B2 | 5/2015 | Just et al. |
| 9,060,756 B2 | 6/2015 | Bencini et al. |
| 9,089,350 B2 | 7/2015 | Willard |
| D736,780 S | 8/2015 | Wang |
| 9,126,023 B1 | 9/2015 | Sahatjian et al. |
| 9,131,980 B2 | 9/2015 | Bloom |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| 9,179,963 B2 | 11/2015 | Ben-Ezra et al. |
| 9,204,929 B2 | 12/2015 | Solis |
| D747,742 S | 1/2016 | Fan et al. |
| D750,644 S | 3/2016 | Bhutani et al. |
| 9,277,960 B2 | 3/2016 | Weinkam et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,314,208 B1 | 4/2016 | Altmann et al. |
| 9,320,631 B2 | 4/2016 | Moore et al. |
| 9,339,331 B2 | 5/2016 | Tegg et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| D783,037 S | 4/2017 | Hariharan et al. |
| 9,655,677 B2 | 5/2017 | Salahieh et al. |
| 9,687,297 B2 | 6/2017 | Just et al. |
| D791,805 S | 7/2017 | Segars |
| 9,693,733 B2 | 7/2017 | Altmann et al. |
| 9,782,099 B2 | 10/2017 | Williams et al. |
| 9,788,895 B2 | 10/2017 | Solis |
| 9,795,442 B2 | 10/2017 | Salahieh et al. |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,907,610 B2 | 3/2018 | Beeckler et al. |
| 9,956,035 B2 | 5/2018 | Govari et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| D861,717 S | 10/2019 | Brekke et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |

(56) References Cited

U.S. PATENT DOCUMENTS

| | | |
|---|---|---|
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,688,278 B2 | 6/2020 | Beeckler et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0111618 A1 | 8/2002 | Stewart et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0093067 A1 | 5/2003 | Panescu |
| 2003/0144658 A1 | 7/2003 | Schwartz et al. |
| 2004/0122445 A1 | 6/2004 | Butler et al. |
| 2004/0147920 A1 | 7/2004 | Keidar |
| 2004/0210121 A1 | 10/2004 | Fuimaono et al. |
| 2004/0225285 A1 | 11/2004 | Gibson |
| 2005/0033135 A1 | 2/2005 | Govari |
| 2005/0070887 A1 | 3/2005 | Taimisto et al. |
| 2005/0119686 A1 | 6/2005 | Clubb |
| 2006/0009689 A1 | 1/2006 | Fuimaono et al. |
| 2006/0009690 A1 | 1/2006 | Fuimaono et al. |
| 2006/0013595 A1 | 1/2006 | Trezza et al. |
| 2006/0025677 A1 | 2/2006 | Verard et al. |
| 2006/0089637 A1 | 4/2006 | Werneth et al. |
| 2006/0100669 A1 | 5/2006 | Fuimaono et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0093806 A1 | 4/2007 | Desai et al. |
| 2007/0276212 A1 | 11/2007 | Fuimaono et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0039790 A1 | 2/2008 | Hasebe |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0234564 A1 | 9/2008 | Beatty et al. |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0221907 A1 | 9/2009 | Bar-Tal |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0222664 A1 | 9/2010 | Lemon et al. |
| 2010/0234746 A1 | 9/2010 | Sebelius |
| 2010/0256629 A1 | 10/2010 | Wylie et al. |
| 2010/0324552 A1 | 12/2010 | Kauphusman et al. |
| 2011/0004087 A1 | 1/2011 | Fish et al. |
| 2011/0028848 A1 | 2/2011 | Shaquer et al. |
| 2011/0118590 A1 | 5/2011 | Zhang |
| 2011/0118632 A1 | 5/2011 | Sinelnikov et al. |
| 2011/0118726 A1 | 5/2011 | De La Rama et al. |
| 2011/0130648 A1 | 6/2011 | Beeckler et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0264000 A1 | 10/2011 | Paul et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0301597 A1 | 12/2011 | McDaniel et al. |
| 2011/0313286 A1 | 12/2011 | Whayne et al. |
| 2012/0017923 A1 | 1/2012 | Sobe |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0130229 A1 | 5/2012 | Zellers et al. |
| 2012/0143177 A1 | 6/2012 | Avitall |
| 2012/0143293 A1 | 6/2012 | Mauch et al. |
| 2012/0172761 A1 | 7/2012 | Meller et al. |
| 2012/0191079 A1 | 7/2012 | Moll et al. |
| 2012/0197100 A1 | 8/2012 | Razavi et al. |
| 2012/0209260 A1 | 8/2012 | Lambert et al. |
| 2012/0323235 A1 | 12/2012 | Danek et al. |
| 2013/0085360 A1 | 4/2013 | Grunewald |
| 2013/0090649 A1 | 4/2013 | Smith et al. |
| 2013/0090651 A1 | 4/2013 | Smith |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0281813 A1 | 10/2013 | Markowitz et al. |
| 2013/0281997 A1 | 10/2013 | Davie |
| 2013/0282084 A1 | 10/2013 | Mathur et al. |
| 2013/0296679 A1 | 11/2013 | Condie et al. |
| 2013/0296852 A1 | 11/2013 | Madjarov et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0025069 A1 | 1/2014 | Willard et al. |
| 2014/0031813 A1 | 1/2014 | Tellio et al. |
| 2014/0051968 A1 | 2/2014 | Isham et al. |
| 2014/0052118 A1 | 2/2014 | Laske et al. |

(56) References Cited

U.S. PATENT DOCUMENTS

| | | |
|---|---|---|
| 2014/0058197 A1 | 2/2014 | Salahieh et al. |
| 2014/0058371 A1 | 2/2014 | Krishnan |
| 2014/0107453 A1 | 4/2014 | Maskara et al. |
| 2014/0121470 A1 | 5/2014 | Scharf et al. |
| 2014/0148805 A1 | 5/2014 | Stewart et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0227437 A1 | 8/2014 | DeBoer et al. |
| 2014/0228838 A1 | 8/2014 | Kirschenman |
| 2014/0243821 A1 | 8/2014 | Salahieh et al. |
| 2014/0257069 A1 | 9/2014 | Eliason et al. |
| 2014/0275993 A1 | 9/2014 | Ballakur |
| 2014/0276712 A1 | 9/2014 | Mallin et al. |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0309512 A1 | 10/2014 | Govari et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0011991 A1 | 1/2015 | Buysman et al. |
| 2015/0025532 A1 | 1/2015 | Hanson et al. |
| 2015/0025533 A1 | 1/2015 | Groff et al. |
| 2015/0045863 A1 | 2/2015 | Litscher et al. |
| 2015/0057519 A1 | 2/2015 | Ben-David et al. |
| 2015/0057655 A1 | 2/2015 | Osypka |
| 2015/0067512 A1 | 3/2015 | Roswell |
| 2015/0080693 A1 | 3/2015 | Solis |
| 2015/0080883 A1 | 3/2015 | Haverkost et al. |
| 2015/0105770 A1 | 4/2015 | Amit |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119670 A1 | 4/2015 | Madjarov et al. |
| 2015/0119875 A1 | 4/2015 | Fischell et al. |
| 2015/0119878 A1 | 4/2015 | Heisel et al. |
| 2015/0133919 A1 | 5/2015 | McDaniel et al. |
| 2015/0141982 A1 | 5/2015 | Lee |
| 2015/0157382 A1 | 6/2015 | Avitall et al. |
| 2015/0157391 A1 | 6/2015 | Ben-Ezra et al. |
| 2015/0208942 A1 | 7/2015 | Bar-Tal et al. |
| 2015/0216591 A1 | 8/2015 | Cao et al. |
| 2015/0216650 A1 | 8/2015 | Shaltis |
| 2015/0238275 A1 | 8/2015 | Kung et al. |
| 2015/0250424 A1 | 9/2015 | Govari et al. |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0270634 A1 | 9/2015 | Buesseler et al. |
| 2015/0272667 A1 | 10/2015 | Govari et al. |
| 2015/0327805 A1 | 11/2015 | Ben-Haim |
| 2015/0327921 A1 | 11/2015 | Govari et al. |
| 2015/0341752 A1 | 11/2015 | Flynn |
| 2015/0342532 A1 | 12/2015 | Basu et al. |
| 2015/0366608 A1 | 12/2015 | Weber et al. |
| 2016/0000499 A1 | 1/2016 | Lennox et al. |
| 2016/0038053 A1 | 2/2016 | Bohorquez et al. |
| 2016/0051321 A1 | 2/2016 | Salahieh et al. |
| 2016/0081746 A1 | 3/2016 | Solis |
| 2016/0085431 A1 | 3/2016 | Kim et al. |
| 2016/0106499 A1 | 4/2016 | Ogata et al. |
| 2016/0113582 A1 | 4/2016 | Altmann et al. |
| 2016/0113709 A1 | 4/2016 | Maor |
| 2016/0166306 A1 | 6/2016 | Pageard |
| 2016/0175041 A1 | 6/2016 | Govari et al. |
| 2016/0183877 A1 | 6/2016 | Williams et al. |
| 2016/0196635 A1 | 7/2016 | Cho et al. |
| 2016/0228023 A1 | 8/2016 | Govari |
| 2016/0228062 A1 | 8/2016 | Altmann et al. |
| 2016/0256305 A1 | 9/2016 | Longo et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2016/0374748 A9 | 12/2016 | Salahieh et al. |
| 2017/0027638 A1 | 2/2017 | Solis |
| 2017/0042614 A1 | 2/2017 | Salahieh et al. |
| 2017/0042615 A1 | 2/2017 | Salahieh et al. |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0080192 A1 | 3/2017 | Giasolli et al. |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0143359 A1 | 5/2017 | Nguyen et al. |
| 2017/0156790 A1 | 6/2017 | Aujla |
| 2017/0164464 A1 | 6/2017 | Weinkam et al. |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0000420 A1 | 1/2018 | Romanowski et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0074693 A1 | 3/2018 | Jones et al. |
| 2018/0085064 A1 | 3/2018 | Auerbach et al. |
| 2018/0110562 A1 | 4/2018 | Govari et al. |
| 2018/0125575 A1 | 5/2018 | Schwartz et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0256247 A1 | 9/2018 | Govari et al. |
| 2018/0279954 A1 | 10/2018 | Hayam et al. |
| 2018/0280080 A1 | 10/2018 | Govari et al. |
| 2018/0296114 A1 | 10/2018 | Welsh et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0333162 A1 | 11/2018 | Saab |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2018/0368927 A1 | 12/2018 | Lyons et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0059818 A1 | 2/2019 | Herrera et al. |
| 2019/0060622 A1 | 2/2019 | Beeckler |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |

(56) References Cited

U.S. PATENT DOCUMENTS

| | | |
|---|---|---|
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0143079 A1 | 5/2019 | Beeckler et al. |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0188909 A1 | 6/2019 | Yellin et al. |
| 2019/0201664 A1 | 7/2019 | Govari |
| 2019/0201669 A1 | 7/2019 | Govari et al. |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0217065 A1 | 7/2019 | Govari et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0297441 A1 | 9/2019 | Dehe et al. |
| 2019/0298441 A1 | 10/2019 | Clark et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2019/0365451 A1 | 12/2019 | Jung, Jr. |
| 2020/0000518 A1 | 1/2020 | Kiernan et al. |
| 2020/0001054 A1 | 1/2020 | Jimenez et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015693 A1 | 1/2020 | Beeckler et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0085497 A1 | 3/2020 | Zhang et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155226 A1 | 5/2020 | Valls et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0169421 A1 | 6/2021 | Govari |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 101422637 A | 5/2009 |
| CN | 101766502 A | 7/2010 |
| CN | 102271607 A | 12/2011 |
| CN | 102458566 A | 5/2012 |
| CN | 103732132 A | 4/2014 |
| CN | 203539434 U | 4/2014 |
| CN | 103860264 A | 6/2014 |
| CN | 104244856 A | 12/2014 |
| CN | 10456117 A | 4/2015 |
| CN | 104783892 A | 7/2015 |
| CN | 104812297 A | 7/2015 |
| CN | 104887294 A | 9/2015 |
| CN | 104936509 A | 9/2015 |
| CN | 105105844 A | 12/2015 |
| CN | 204814163 U | 12/2015 |
| CN | 105473091 A | 4/2016 |
| CN | 105473093 A | 4/2016 |
| CN | 111248993 A | 6/2020 |
| CN | 111248996 A | 6/2020 |
| EP | 0668740 A1 | 8/1995 |
| EP | 0779059 A1 | 6/1997 |
| EP | 0644738 B1 | 3/2000 |
| EP | 0727183 B1 | 11/2002 |
| EP | 0727184 B1 | 12/2002 |
| EP | 1790304 A2 | 5/2007 |
| EP | 2682157 A1 | 1/2014 |
| EP | 2749214 A1 | 7/2014 |
| EP | 2783651 A1 | 10/2014 |
| EP | 28665350 A2 | 4/2015 |
| EP | 2875790 A2 | 5/2015 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 3238646 A2 | 11/2017 |
| EP | 3238648 A1 | 11/2017 |
| EP | 3251622 A1 | 12/2017 |
| EP | 2884931 B1 | 1/2018 |
| EP | 3300680 A1 | 4/2018 |
| EP | 3315087 A1 | 5/2018 |
| EP | 3332727 A2 | 6/2018 |
| EP | 2349440 B1 | 8/2019 |
| EP | 3571983 A2 | 11/2019 |
| EP | 3318211 B1 | 12/2019 |

(56) References Cited

FOREIGN PATENT DOCUMENTS

| | | |
|---|---|---|
| EP | 3581135 A1 | 12/2019 |
| EP | 3586778 A1 | 1/2020 |
| EP | 2736434 B1 | 2/2020 |
| EP | 3451962 B1 | 3/2020 |
| EP | 3653153 A1 | 5/2020 |
| EP | 3972510 A1 | 3/2022 |
| JP | H06205837 A | 7/1994 |
| JP | H1176183 A | 3/1999 |
| JP | H1176233 A | 3/1999 |
| JP | H06261951 A | 3/1999 |
| JP | 2000504242 A | 4/2000 |
| JP | 2002345765 A | 12/2002 |
| JP | 2005052424 A | 3/2005 |
| JP | 2005525162 A | 8/2005 |
| JP | 2006511296 A | 4/2006 |
| JP | 2008508064 A | 3/2008 |
| JP | 2010507404 A | 3/2010 |
| JP | 2010522623 A | 7/2010 |
| JP | 2011500172 A | 1/2011 |
| JP | 2011152430 A | 8/2011 |
| JP | 2012024156 A | 2/2012 |
| JP | 2013013726 A | 1/2013 |
| JP | 2013078587 A | 5/2013 |
| JP | 2013529109 A | 7/2013 |
| JP | 2013531525 A | 8/2013 |
| JP | 2014506171 A | 3/2014 |
| JP | 2014507197 A | 3/2014 |
| JP | 2014529419 A | 11/2014 |
| JP | 2014530039 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015134166 A | 7/2015 |
| JP | 2015518776 A | 7/2015 |
| JP | 2015139707 A | 8/2015 |
| JP | 2015167864 A | 9/2015 |
| JP | 2016515442 A | 5/2016 |
| JP | 2016116863 A | 6/2016 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0053237 A2 | 9/2000 |
| WO | 0182814 A2 | 11/2001 |
| WO | 02102231 A2 | 12/2002 |
| WO | 2004087249 A2 | 10/2004 |
| WO | 22005041748 A2 | 5/2005 |
| WO | 2008049087 A2 | 4/2008 |
| WO | 2011143468 A2 | 11/2011 |
| WO | 2012/092016 A1 | 7/2012 |
| WO | 2012100185 A2 | 7/2012 |
| WO | 2013049601 A2 | 4/2013 |
| WO | 2013052852 A1 | 4/2013 |
| WO | 2013052919 A2 | 4/2013 |
| WO | 2013154776 A2 | 10/2013 |
| WO | 2013162884 A1 | 10/2013 |
| WO | 2013173917 A1 | 11/2013 |
| WO | 2013176881 A1 | 11/2013 |
| WO | 2014168987 A1 | 10/2014 |
| WO | 2014176205 A1 | 10/2014 |
| WO | 2015049784 A1 | 4/2015 |
| WO | 2016019760 A1 | 2/2016 |
| WO | 2016044687 A1 | 3/2016 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018111600 A1 | 6/2018 |
| WO | 2018129133 A1 | 7/2018 |
| WO | 2018191149 A1 | 10/2018 |
| WO | 2019084442 A1 | 5/2019 |
| WO | 2019095020 A1 | 5/2019 |
| WO | 2019143960 A1 | 7/2019 |
| WO | 2020026217 A1 | 2/2020 |
| WO | 2020206328 A1 | 10/2020 |

OTHER PUBLICATIONS

First Office Action dated Apr. 6, 2021, from corresponding CN Application No. 201710433124.2.
First Office Action dated Nov. 10, 2021, from corresponding CN Application No. 201710433124.2.
First Office Action dated Nov. 10, 2021, from corresponding CN Application No. 201710433114.9.
Extended European Search Report dated Jun. 26, 2020, from corresponding EP Appl. No. 20150359.6.
Notification of Reasons for Refusal dated Jun. 1, 2021, from corresponding JP2017-113536.
Notification of Reasons for Refusal dated Jul. 6, 2021, from corresponding JP2017-113535.
Notification of Reasons for Refusal dated Feb. 22, 2022, from corresponding JP2017-113535.
Notification of Reasons for Refusal dated Mar. 15, 2022, from corresponding JP2017-113536.
Notification of Reasons for Refusal dated Aug. 30, 2022, from corresponding JP2017-113535.
Extended European Search Reporte dated Feb. 6, 2018, from corresponding EP Appl. No. 17174936.9.
Partial European Search Reporte dated Oct. 24, 2017, from corresponding EP Appl. No. 17174936.9.
European Search Reporte dated Aug. 9, 2019, from corresponding EP Appl. No. 17175072.2.
European Search Reporte dated Dec. 11, 2018, from corresponding EP Appl. No. 17175072.2.
Extended European Search Report dated Oct. 20, 2017, from corresponding EP Appl. No. 17175072.2.
Extended European Search Report dated Dec. 12, 2018, from corresponding EP Appl. No. 18192797.1.
Search Report dated Dec. 8, 2020, from corresponding CN Application No. 201710433114.
Supplementary Search Report dated Jun. 27, 2021, from corresponding CN Application No. 201710433114.
Second Office Action dated Jul. 2, 2021, from corresponding CN Application No. 201710433114.
Supplementary Search Report dated Nov. 2, 2021, from corresponding CN Application No. 201710433124.
Maury P., et al., "Three-dimensional Mapping in the Electrophysiological Laboratory," Archives of Cardiovascular Disease, Published Jun. 7, 2018, vol. 111, pp. 456-464, https://doi.org/10.1016/j.acvd,2018,03.013, Retrieved from URL: https://www.sciencedirect.com/science/article/pii/S1875213618300901.
Article 94(3) Communication dated Aug. 9, 2019, from corresponding EP Appl. No. 17175072.2.
First Office Action dated Dec. 15, 2020, from corresponding Chinese Application No. 2017104331149.
Search Report dated May 19, 2021, from corresponding Japanese Application. No. JP2017-113536.
Search Report dated May 31, 2021, from corresponding Japanese Application. No. JP2017-113535.
Notice of Reasons for Refusal dated Jul. 6, 2021, from corresponding Japanese Application. No. JP2017-113535.
Supplemental Search from corresponding Chinese Application No. 2017104331149 dated Nov. 3, 2021.
Second Office Action dated Nov. 10, 2021, from corresponding CN Application No. 201710433124.2.
Third Office Action from corresponding Chinese Application No. 2017104331149 dated Dec. 2, 2021.
Supplementary Search from corresponding Chinese Application No. 2017104331242 dated Apr. 13, 2022.
Third Office Action dated Apr. 20, 2022, from corresponding Chinese Application No. 2017104331242.
Supplementary Search from corresponding Chinese Application No. 2017104331242 dated Jul. 5, 2022.

(56) References Cited

OTHER PUBLICATIONS

Fourth Office Action from corresponding Chinese Application No. 2017104331149 dated Aug. 8, 2022.
Article 94(3) communication dated Jul. 11, 2023, from corresponding European Application No. 20190495.0.
First Search from corresponding Chinese Application No. 2017104331242 dated Mar. 26, 2021.
Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.
Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.
Co-Pending U.S. Appl. No. 14/578,807, filed Dec. 22, 2014, 21 pages.
Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.
Dorobantu M., et al., "Oral Anticoagulation During Atrial Fibrillation Ablation: Facts and Controversies," Cor et Vasa, 2013, Accepted on Dec. 3, 2012, vol. 55, No.2, pp. e101-e106, Retrieved from URL: https://www.sciencedirect.com/science/article/pii/s0010865012001415.
Extended European Search Report for Application No. EP17168513.4 mailed Sep. 18, 2017, 11 pages.
Extended European Search Report for European Application No. 15201723.2, mailed May 11, 2016, 7 pages.
Extended European Search Report for European Application No. 17168393.1 mailed Dec. 15, 2017, 12 Pages.
Extended European Search Report for European Application No. 17168518.3, mailed Sep. 20, 2017, 9 Pages.
Extended European Search Report for European Application No. 17173893.3, mailed Nov. 6, 2017, 8 Pages.
Extended European Search Report for European Application No. 17201434.2, mailed Feb. 1, 2018, 10 Pages.
Extended European Search Report for European Application No. 17205876.0, mailed Jun. 1, 2018, 13 Pages.
Extended European Search Report for European Application No. 19177365.4, mailed Nov. 8, 2019, 07 Pages.
Extended European Search Report for European Application No. 19183327.6, mailed Nov. 21, 2019, 8 Pages.
Extended European Search Report for European Application No. 20153872.5, mailed May 7, 2020, 9 Pages.
Extended European Search Report for European Application No. 20195648.9, mailed Feb. 12, 2021, 9 Pages.
Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.
Haines D.E., et al., "The Promise of Pulsed Field Ablation," Dec. 2019, vol. 19, No. 12, 10 Pages.
Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.
International Search Report and Written Opinion for International Application No. PCT/IB2019/052313, mailed Jul. 22, 2019, 8 Pages.
International Search Report and Written Opinion for International Application No. PCT/IB2019/056381, mailed Dec. 17, 2019, 10 Pages.
International Search Report and Written Opinion for International Application No. PCT/IB2019/057743, mailed Dec. 6, 2019, 16 Pages.
International Search Report and Written Opinion issued in corresponding International Application No. PCT/IB2019/057742, dated Nov. 28, 2019, 18 Pages.
Nagashima K., et al., "Hot Balloon Versus Cryoballoon Ablation for Atrial Fibrillation," Circulation: Arrhythmia and Electrophysiology, May 2018, Vol. 11, No. 5, e005861, 9 Pages.
Napoli N., et al., "For Atrial Fibrillation Abalation, Newer Anticoagulant Reduces Major Bleeds," American Collage of Cardiology, Mar. 19, 2017, 4 Pages, [Retrieved on Jan 1, 2022] Retrieved from URL: http://www.acc.org/about-acc/press-releases/2017/03/18/08/47/sun-1045am-for-atrial-fibrillation-ablation-newer-anticoagulant-reduces-major-bleeds.
Okano T., et al., "Wire Perforation Causing Cardiopulmonary Arrest During Radiofrequency Hot Balloon Ablation for Pulmonary Vein Isolation,"Journal of Cardiology Cases, Feb. 15, 2019, vol. 19, No. 5, pp. 169-172.
Partial European Search Report for European Application No. 17168393.1 mailed Sep. 13, 2017, 13 Pages.
Partial European Search Report for European Application No. 17205876.0, mailed Feb. 22, 2018, 10 Pages.
Reddy V.Y., et al., "Ballon Catherer Ablation to Treat Proxysmal Atrial Fibrillation: What is the Level of Pulmonary Venous Isolation? ," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11. No. 6, pp. 963-968.
Youtube:, "Intensity™ CX4 Professional E-Stim/ Ultrasound Combo," Dec. 22, 2015, 1 Page, [Retrieved on Nov. 19, 2020], Retrieved from URL: http://www.youtube.com/watch?v=76s1QkMWJME].
Youtube: "New Interface TactiCath Contact Force Ablation Catheter,"Nov. 26, 2013, 1 Pages, [Retrieved on Nov. 19, 2020], Retrieved from URL: https: /Avww.youtube.com/watch?v= aTvYO8Hpylg].

MULTI-FUNCTION CONDUCTING ELEMENTS FOR A CATHETER

CROSS-REFERENCE TO RELATED APPLICATIONS

The present application is a continuing application under 35 USC § 120 and claims the benefits of prior U.S. patent application Ser. No. 15/359,838 filed Nov. 23, 2016, now allowed, which prior application is a continuation-in-part of, and claims the benefit of, U.S. patent application Ser. No. 15/177,775, entitled "Dual-function sensors for a basket catheter," filed Jun. 9, 2016, whose disclosure is incorporated herein by reference.

FIELD OF THE INVENTION

Embodiments of the present invention relate generally to the field of medical devices, and particularly to catheters for recording intracardiac electrocardiogram (ECG) signals and/or ablating cardiac tissue.

BACKGROUND

In some applications, a basket catheter, comprising a large number of electrodes disposed on a plurality of splines, is used to acquire intracardiac electrocardiogram (ECG) signals. Such signals may be used, for example, to construct an electroanatomical map of the heart.

In other applications, a balloon catheter, comprising a plurality of electrodes disposed on a balloon, is used to ablate cardiac tissue, and/or to acquire intracardiac ECG signals.

US Patent Application Publication 2011/0118590, whose disclosure is incorporated herein by reference, describes an interventional system for internal anatomical examination that includes a catheterization device for internal anatomical insertion. The catheterization device includes at least one magnetic field sensor for generating an electrical signal in response to rotational movement of the at least one sensor about an axis through the catheterization device within a magnetic field applied externally to patient anatomy, and a signal interface for buffering the electrical signal for further processing. A signal processor processes the buffered electrical signal to derive a signal indicative of angle of rotation of the catheterization device relative to a reference. The angle of rotation is about an axis through the catheterization device. A reproduction device presents a user with data indicating the angle of rotation of the catheterization device.

US Patent Application Publication 2003/0093067, whose disclosure is incorporated herein by reference, describes systems and methods for imaging a body cavity and for guiding a treatment element within a body cavity. A system may include an imaging subsystem having an imaging device and an image processor that gather image data for the body cavity. A mapping subsystem may be provided, including a mapping device and a map processor, to identify target sites within the body cavity, and provide location data for the sites. The system may also include a location processor coupled to a location element on a treatment device to track the location of the location element. The location of a treatment element is determined by reference to the location element. A treatment subsystem including a treatment device having a treatment element and a treatment delivery source may also be provided. A registration subsystem receives and registers data from the other subsystems, and displays the data.

U.S. Pat. No. 6,272,371, whose disclosure is incorporated herein by reference, describes an invasive probe apparatus including a flexible elongate probe having a distal portion adjacent to a distal end thereof for insertion into the body of a subject, which portion assumes a predetermined curve form when a force is applied thereto. First and second sensors are fixed to the distal portion of the probe in known positions relative to the distal end, which sensors generate signals responsive to bending of the probe. Signal processing circuitry receives the bend responsive signals and processes them to find position and orientation coordinates of at least the first sensor, and to determine the locations of a plurality of points along the length of the distal portion of the probe.

US Patent Application Publication 2006/0025677, whose disclosure is incorporated herein by reference, describes a surgical navigation system for navigating a region of a patient that may include a non-invasive dynamic reference frame and/or fiducial marker, sensor tipped instruments, and isolator circuits. The dynamic reference frame may be placed on the patient in a precise location for guiding the instruments. The dynamic reference frames may be fixedly placed on the patient. Also the dynamic reference frames may be placed to allow generally natural movements of soft tissue relative to the dynamic reference frames. Also methods are provided to determine positions of the dynamic reference frames. Anatomical landmarks may be determined intra-operatively and without access to the anatomical structure.

U.S. Pat. No. 6,892,091, whose disclosure is incorporated herein by reference, describes an apparatus and method for rapidly generating an electrical map of a chamber of a heart that utilizes a catheter including a body having a proximal end and a distal end. The distal end has a distal tip and an array of non-contact electrodes having a proximal end and a distal end and at least one location sensor. Preferably, two location sensors are utilized. The first location sensor is preferably proximate to the catheter distal tip and the second location sensor is preferably proximate to the proximal end of the non-contact electrode array. The catheter distal end further preferably includes a contact electrode at its distal tip. Preferably, at least one and preferably both of the location sensors provide six degrees of location information. The location sensor is preferably an electromagnetic location sensor. The catheter is used for rapidly generating an electrical map of the heart within at least one cardiac cycle and preferably includes cardiac ablation and post-ablation validation.

SUMMARY OF THE INVENTION

There is provided, in accordance with some embodiments of the present invention, apparatus that includes an expandable structure, configured for insertion into a body of a subject, and a plurality of conducting elements coupled to the expandable structure. Each of the conducting elements includes a respective coil, and has an insulated portion that is electrically insulated from tissue of the subject, and an uninsulated portion configured to exchange signals with the tissue, while in contact with the tissue.

In some embodiments, the expandable structure includes a balloon.

In some embodiments, the expandable structure includes a basket.

In some embodiments, each of the conducting elements includes an electrode connected to the coil, the electrode being configured to exchange the signals with the tissue, and the coil being configured to carry the exchanged signals.

In some embodiments, the coil is situated proximally to the electrode to which the coil is connected.

In some embodiments, the coil is a single-loop coil.

In some embodiments, the coil is a helical coil.

In some embodiments, the coil is flat.

In some embodiments, the apparatus further includes two leads connected to each conducting element of the conducting elements, configured to carry the signals between the conducting element and a proximal end of the apparatus.

In some embodiments, at least part of each conducting element of the conducting elements has an electrical resistance that varies in response to strain to which the conducting element is subjected inside the body of the subject.

In some embodiments, each of the conducting elements includes a thermocouple junction.

In some embodiments, the coil includes the uninsulated portion.

There is further provided, in accordance with some embodiments of the present invention, a method that includes receiving from a conducting element, via two leads that connect the conducting element to a proximal end of a catheter, a voltage difference that was induced across the conducting element by a magnetic field. The method further includes, in response to the voltage difference, ascertaining a location of the conducting element, and, while the conducting element is in contact with tissue of a subject, exchanging a signal with the tissue via the conducting element and at least one of the leads.

In some embodiments, the signal is an electrocardiogram (ECG) signal, and exchanging the signal includes acquiring the ECG signal from the tissue.

In some embodiments, the signal is an ablation signal, and exchanging the signal includes passing the ablation signal into the tissue.

In some embodiments, exchanging the signal includes exchanging the signal while the conducting element is inside a body of a subject.

In some embodiments, the conducting element is a single-loop coil.

In some embodiments, the conducting element is a helical coil.

In some embodiments, the voltage difference is a first voltage difference, and the method further includes measuring a temperature, by measuring a second voltage difference across the leads.

In some embodiments, the method further includes measuring a strain exerted on the conducting element, by measuring an electrical resistance of the conducting element.

In some embodiments, the method further includes measuring an impedance between the conducting element and a patch coupled to skin of the subject, by passing an electric current between the conducting element and the patch, wherein the ascertaining of the location is further in response to the measured impedance.

The present invention will be more fully understood from the following detailed description of embodiments thereof, taken together with the drawings, in which:

DETAILED DESCRIPTION OF EMBODIMENTS

Overview

Embodiments described herein include catheters comprising conducting elements that perform, e.g., simultaneously, a plurality of functions. For example, the conducting elements may function as electromagnetic sensors, by outputting, in the presence of a magnetic field, signals that may be used to ascertain the location and/or orientation of the catheter on which the conducting elements are disposed. In addition, the conducting elements may function as electrodes. For example, the conducting elements may be used to exchange signals with tissue, such as by acquiring ECG signals from tissue, or passing ablating signals into tissue. Alternatively or additionally, the conducting elements may be used to measure impedance, temperature, strain, and/or other relevant parameters.

More particularly, embodiments described herein include a basket catheter that may be used, for example, to build an electroanatomical map. The basket catheter comprises a plurality of splines at its distal end, and further comprises a plurality of helical conducting elements, which are disposed on the splines. During the electroanatomical mapping procedure, the helical conducting elements function as inductors, in that a generated magnetic field induces respective voltage differences across the conducting elements. Based on the induced voltage differences, the respective locations and orientations of the conducting elements—and hence, the location and orientation of the basket catheter—may be precisely determined.

The helical conducting elements additionally function as electrodes for acquiring ECG signals, such that it may not be necessary to equip the basket catheter with separate ECG-acquiring electrodes. For example, an electrically-insulative layer may cover the majority of each of the helical conducting elements, but leave a small portion of each of the helical conducting elements exposed. This exposed portion, when brought into contact with the intracardiac tissue, acquires ECG signals from the tissue.

The helical conducting elements described herein may thus function in two capacities—e.g., simultaneously—during a single procedure. First, they may function as ECG electrodes, by sensing the intracardiac ECG signals. Second, they may function as magnetic-field sensors, by outputting location-indicating signals (in the form of the above-described induced voltages) in response to the generated magnetic field. The conducting elements may thus be described as ECG electrodes that additionally function as magnetic-field sensors, or as magnetic-field sensors that additionally function as ECG electrodes. (Notwithstanding the above, in some embodiments, the conducting elements are used only as magnetic-field sensors, and separate electrodes coupled to the splines are used to acquire the ECG signals.)

Other embodiments described herein include a balloon catheter, comprising a balloon, and a plurality of conducting elements coupled to the balloon. Each one of the conducting elements comprises an electrode, configured to exchange signals with tissue, and a coil that is connected to the electrode. The coil carries the signals that are exchanged with the tissue, and also outputs signals (in the form of induced voltages) in response to a magnetic field. The conducting elements thus function as both magnetic-field sensors and as electrodes. Alternatively or additionally, the conducting elements may measure other parameters, such as impedance, temperature, or strain.

Embodiments described herein further include circuitry for processing signals received from the multi-function conducting elements. For example, the circuitry described herein may generate, based on signals received from the above-described helical conducting elements, a plurality of outputs, which are used by a processor to construct an electroanatomical map. These outputs include a plurality of first outputs, which indicate the electrical activity of the tissue, a plurality of second outputs, which indicate the respective induced voltage differences across the conducting elements, and a plurality of third outputs, which indicate the proximity to the tissue of each of the conducting elements.

Apparatus Description

Figure 1:
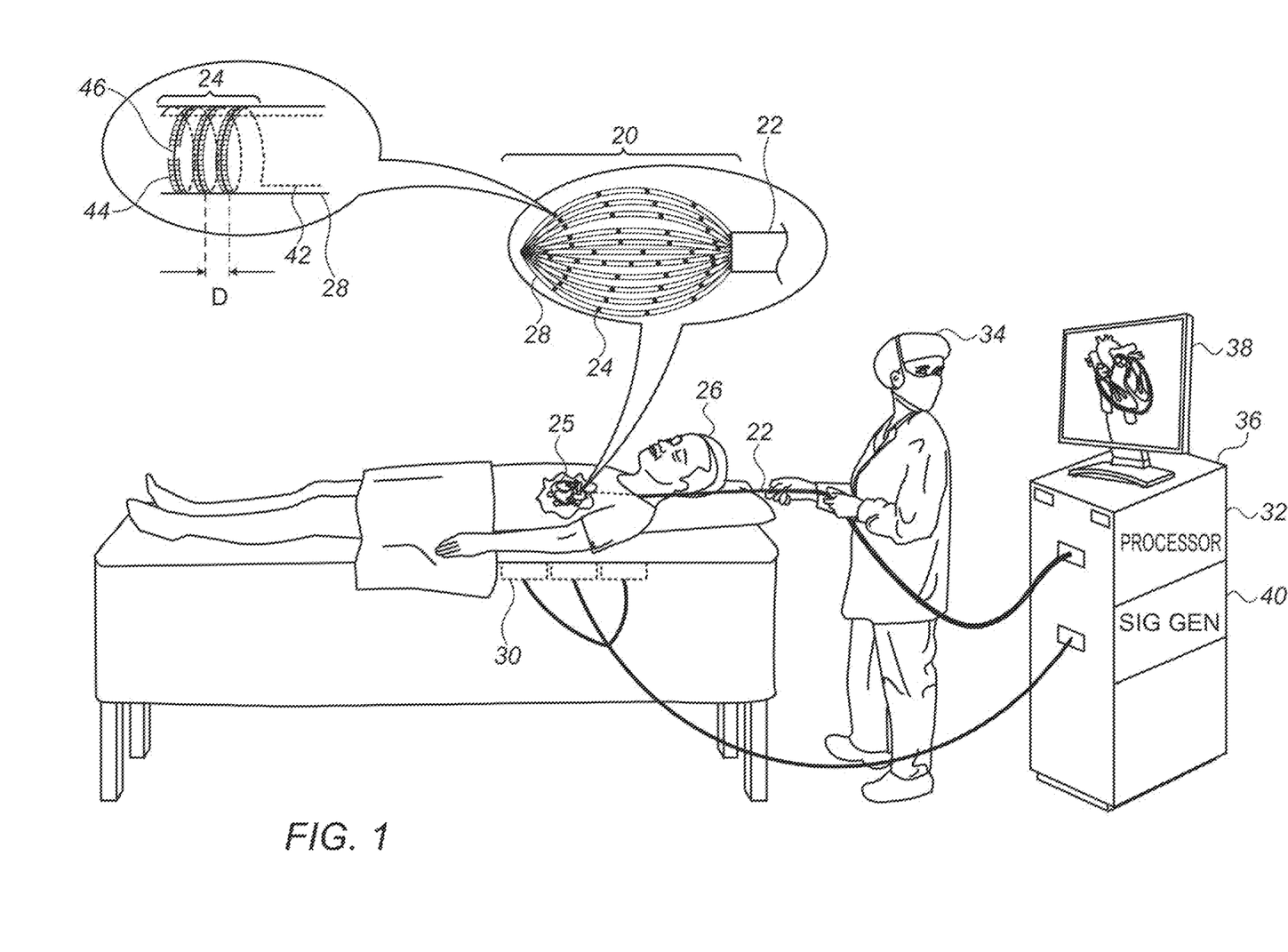
FIG. 1 is a schematic illustration of a basket catheter, in accordance with some embodiments of the present invention.

Reference is initially made to FIG. 1, which is a schematic illustration of a basket catheter 22, in accordance with some embodiments of the present invention. FIG. 1 depicts a physician 34 using basket catheter 22 to perform an electroanatomical mapping of a heart 25 of a subject 26. During the mapping procedure, the distal end of the catheter, which comprises a basket 20 of splines 28, is inserted into heart 25. The splines are then brought into contact with the intracardiac tissue, and conducting elements 24 on the splines acquire intracardiac ECG signals. A console 36, which is connected to the basket catheter and comprises a computer processor 32, receives these ECG signals.

While the intracardiac ECG signals are being acquired, a magnetic field is generated by a plurality of magnetic-field generators 30 located underneath subject 26 or otherwise in the vicinity of the subject. (As shown in FIG. 1, a signal generator ("SIG GEN") 40 in console 36 may cause generators 30 to generate the magnetic field by supplying an alternating current to the generators.) The magnetic field induces voltage differences across conducting elements 24. The induced voltage differences are received by the console, and, based on the induced voltages, processor 32 ascertains the position of each of the conducting elements. Processor 32 then constructs an electroanatomical map of the heart, based on the ECG signals (which indicate the electrical activity of the intracardiac tissue) and the voltages received from the helical conducting elements (which indicate the respective locations of the sources of the ECG signals). Such a map may be displayed on a monitor 38 for viewing by physician 34, and/or stored for later analysis.

Splines 28 may be arranged to define any suitably-shaped basket, such as the spheroidal basket shown in FIG. 1. FIG. 1 shows an embodiment in which a plurality of helical conducting elements 24 are disposed on the surface of each of the splines. The top-left portion of the figure shows an enlarged view of a single such helical conducting element. In this enlarged view, the solid portion of the conducting element corresponds to the portion of the conducting element that is on the near side of the spline, facing the viewer. The dotted portion corresponds to the portion of the conducting element that is on the far side of the spline, facing away from the viewer. Each of the two terminals of each of the conducting elements is typically connected to the console via a wire 42 which passes through the interior of the spline.

In some embodiments, the conducting elements are printed onto the splines. For example, each of the conducting elements may comprise electrically-conductive paint that is helically painted onto the splines. In other embodiments, the conducting elements comprise wires that are wound (i.e., coiled) around, and glued or otherwise attached to, the splines. In any case, for embodiments in which the helical conducting elements are on the surface of the splines, an electrically-insulative layer 44 typically covers at least a majority of each of the helical conducting elements. Electrically-insulative layer 44 prevents the turns of any given conducting element from being shorted with each other.

Typically, the electrically-insulative layer does not cover a portion of exactly one respective turn of each of the helical conducting elements. Thus, the electrically-insulative layer prevents shorting of the turns (in that no more than one turn of each conducting element is exposed), but also allows the conducting elements to acquire ECG signals. For example, the enlarged portion of FIG. 1 shows an embodiment in which the electrically-insulative layer exposes a portion 46 of the conducting element. Exposed portion 46 may be brought into contact with tissue, in order to acquire an ECG signal.

As noted above, the exposed portion of the conducting element is confined to one turn of the conducting element. This means that the distance between the distalmost exposed portion of the conducting element and the proximal most exposed portion of the conducting element is less than the distance D that separates between successive turns of the conducting element.

In some embodiments, the electrically-insulative layer is contiguous across a plurality of conducting elements. In other embodiments, as depicted in FIG. 1, the electrically-insulative layer is discontiguous, such that no portion of the electrically-insulative layer covers more than one of the conducting elements. Similarly, for any given conducting element, the cover provided by the electrically-insulative layer may be contiguous or discontiguous. As an example of the latter, in FIG. 1, the conducting element is covered by two separate, disjoint portions of the electrically-insulative layer, these portions being on respective opposite sides of exposed portion 46 of the conducting element.

In some embodiments, alternatively to being disposed on the splines as in FIG. 1, the conducting elements are contained within the splines. In such embodiments, the splines, being made of an electrically-insulative material (such as plastic), provide the "cover" that prevents the conducting elements from being shorted. For embodiments in which the conducting elements are additionally used to acquire ECG signals, the splines are shaped to define a plurality of openings that expose a portion of exactly one respective turn of each of the helical conducting elements. In other words, such embodiments are analogous to the embodiments described above, with the surface of the spline functioning analogously to electrically-insulative layer 44 in preventing shorting of the conducting elements, but also, optionally, providing for ECG-signal acquisition.

Figure 2:
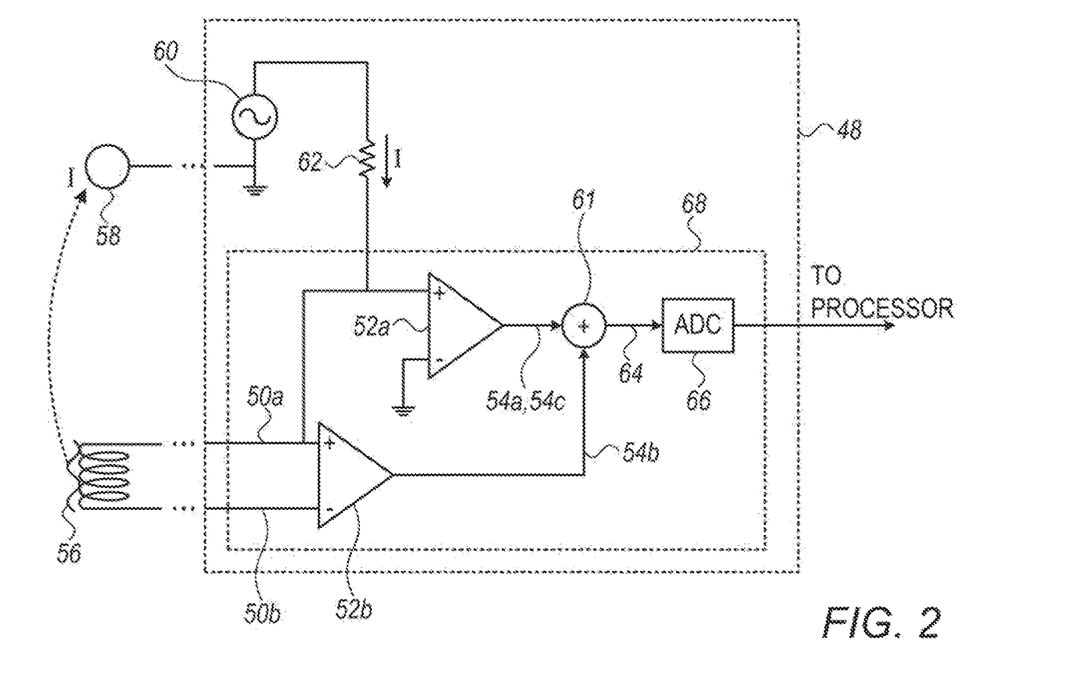
FIGS. 2-3 are schematic illustrations of circuitry for processing signals received from conducting elements, in accordance with some embodiments of the present invention.

Reference is now made to FIG. 2, which is a schematic illustration of circuitry 48 for processing signals received from conducting elements 24, in accordance with some embodiments of the present invention. Circuitry 48 is typically located within console 36, between the catheter-console interface and the processor. As shown in FIG. 2, circuitry 48 is connected to each helical conducting element 24, typically via exactly two connections (or "leads") connected to the conducting element: a first connection 50a to one terminal of the conducting element, and a second connection 50b to the other terminal of the conducting element. As further described below, circuitry 48 generates outputs based on signals received, via connections 50a and 50b, from each helical conducting element. Based on these outputs, processor 32 constructs an electroanatomical map of the subject's heart.

Typically, circuitry 48 comprises a first differential amplifier 52a and a second differential amplifier 52b. Connections 50a and 50b are connected to second differential amplifier 52b, while one of the connections—e.g., first connection 50a—is also connected to first differential amplifier 52a. Connections 50a and 50b thus carry inputs to the differential amplifiers, as further described below.

As described above, the exposed portion of each conducting element 24 is brought into contact with intracardiac tissue 56, such that an ECG voltage (referred to above as an "ECG signal") is transferred to the conducting element from the tissue. (The ECG voltage is generally constant across the conducting element, i.e., the ECG voltage at the terminal of the conducting element is not significantly different from the ECG voltage at the exposed portion of the conducting element.) First connection 50a carries the ECG voltage to first differential amplifier 52a, which generates a first output 54a based on the ECG voltage, by amplifying a difference between the received ECG voltage and a reference voltage. The processor derives electrical-activity information from first output 54a, and uses this information to build the electroanatomical map. Typically, the reference voltage is the voltage at a reference electrode 58 disposed on the basket catheter, e.g., on a central spline of the catheter shaft (not shown in FIG. 1). (In FIG. 2, reference electrode 58 is connected to ground, such that the reference voltage is ground.)

Connection 50a also carries, to second differential amplifier 52b, the voltage induced by the magnetic field at one terminal of the conducting element, while connection 50b carries the voltage induced at the other terminal. In other words, connections 50a and 50b collectively carry, to the second differential amplifier, the voltage difference that is induced across the conducting element. Based on this voltage difference, second differential amplifier 52b generates a second output 54b, by amplifying the voltage difference. Second output 54b includes anatomical information, in that the second output indicates the position of the conducting element, and hence, the location of the source of the ECG signal. The processor derives this anatomical information from the second output, and then, in building the electroanatomical map, combines this anatomical information with the electrical-activity information derived from the first output.

Typically, circuitry 48 further comprises a current source, or, as in FIG. 2, a voltage source 60 in series with a resistor 62, which together function as a current source. The current source passes a current "I" over connection 50a and between the conducting element and reference electrode 58 (or a different reference electrode that is not used for the ECG reference voltage). During the passing of the current, the voltage on the conducting element indicates the impedance that is seen by the conducting element; the higher the voltage, the higher the impedance. The impedance, in turn, indicates the proximity of the conducting element to the tissue; the higher the impedance, the greater the proximity. Thus, the voltage on the conducting element indicates the proximity of the conducting element to the tissue. The first differential amplifier generates a third output 54c based on this proximity-indicating voltage, by amplifying the difference between the proximity-indicating voltage and the reference voltage. The processor then uses the third output to build the electroanatomical map. In particular, the processor first derives, from the third output, the proximity of the conducting element to the tissue. The processor then decides whether to accept the first (electrical-activity-related) output, based on the proximity. For example, the processor may compare the proximity to a threshold, and accept the first output only if the proximity is greater than the threshold (i.e., the distance between the conducting element and the tissue is sufficiently small).

It is noted that the ECG voltage, the induced voltage, and the proximity-indicating voltage are of sufficiently different frequencies, such that the three voltages may be simultaneously carried on connection 50a (and hence, simultaneously received by the circuitry). Thus, first output 54a, second output 54b, and third output 54c may be generated at the same time. In some embodiments, an adder 61 adds the first output, the second output, and the third output, yielding a combined output 64 having a plurality of components at various frequencies. Combined output 64 is then passed to an analog-to-digital converter (ADC) 66, which converts the combined output to a digital signal that is passed to the processor.

Although, for simplicity, only a single helical conducting element 24 is shown in FIG. 2, basket catheter 22 typically comprises a large number of helical conducting elements. On this note, reference is now made to FIG. 3, which is a schematic illustration of circuitry 48, in accordance with some embodiments of the present invention.

Figure 3:
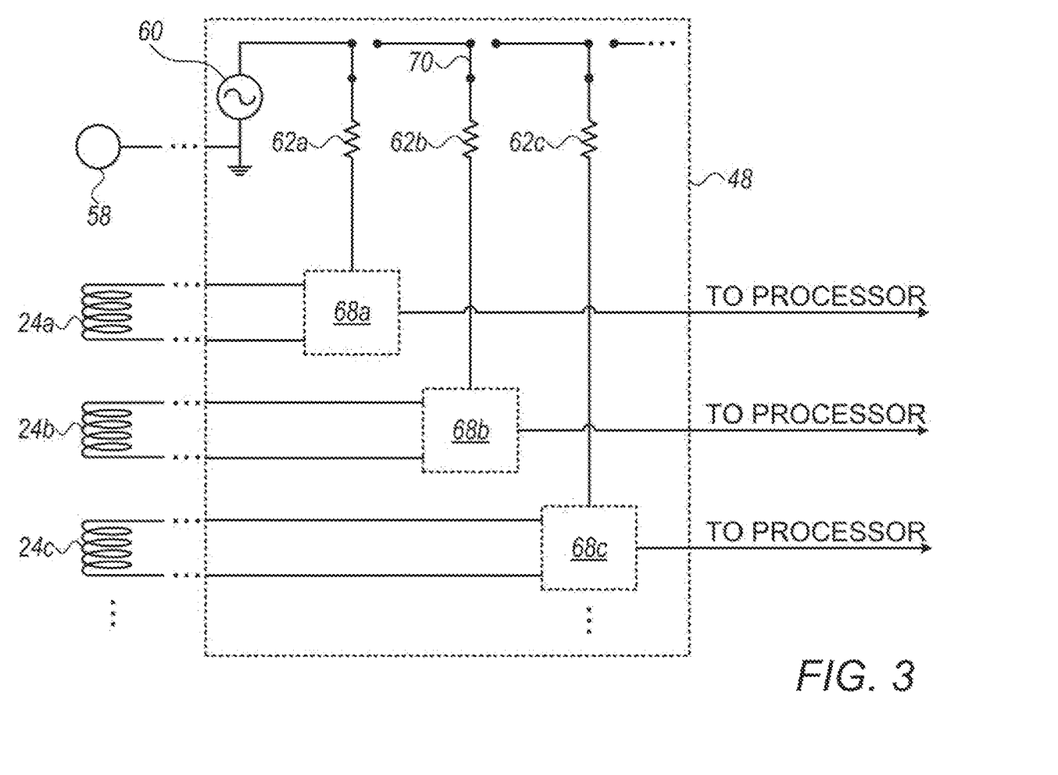

FIG. 3 shows a way in which the configuration of circuitry 48 shown in FIG. 2 may be extended to handle a large number of inputs from a large number of helical conducting elements. In particular, in FIG. 3, a block 68 of circuitry that is shown in FIG. 2 is replicated for each of the conducting elements. Thus, in FIG. 3, a conducting element 24a connects to a block 68a of circuitry, a conducting element 24b connects to a block 68b, and a conducting element 24c connects to a block 68c. Similarly, resistor 62 is replicated for each of the conducting elements, such that voltage source 60 may be connected to block 68a via a resistor 62a, to block 68b via a resistor 62b, or to block 68c via a resistor 62c. (Typically, switches 70 ensure that the voltage source is connected to no more than one block at a time.) Thus, for example, to pass a current between conducting element 24a and the reference electrode, the voltage source is connected to block 68a.

As indicated by the three-dot sequences in the figure, the configuration shown in FIG. 3 may be extended to handle any number of conducting elements.

It is emphasized that the principles described herein may be applied in many ways. For example, the scope of the present disclosure includes using each of one or more coils, and/or other conducting elements, for both (i) magnetic tracking, and (ii) exchanging signals with tissue, in any relevant application. (Circuitry described with reference to FIGS. 2-3 may be modified as appropriate to suit the application.) Exchanging signals with tissue includes, for example, acquiring ECG signals as described above, and/or passing ablating signals into tissue. (In the latter case, the same leads that carry the induced voltage from the conducting element may be used to deliver the ablating signal to the conducting element.) Moreover, the multi-function sensors described herein may be disposed on any suitable apparatus, including, for example, an intrabody device such as a lasso catheter, balloon catheter, or other type of catheter.

Figure 4:
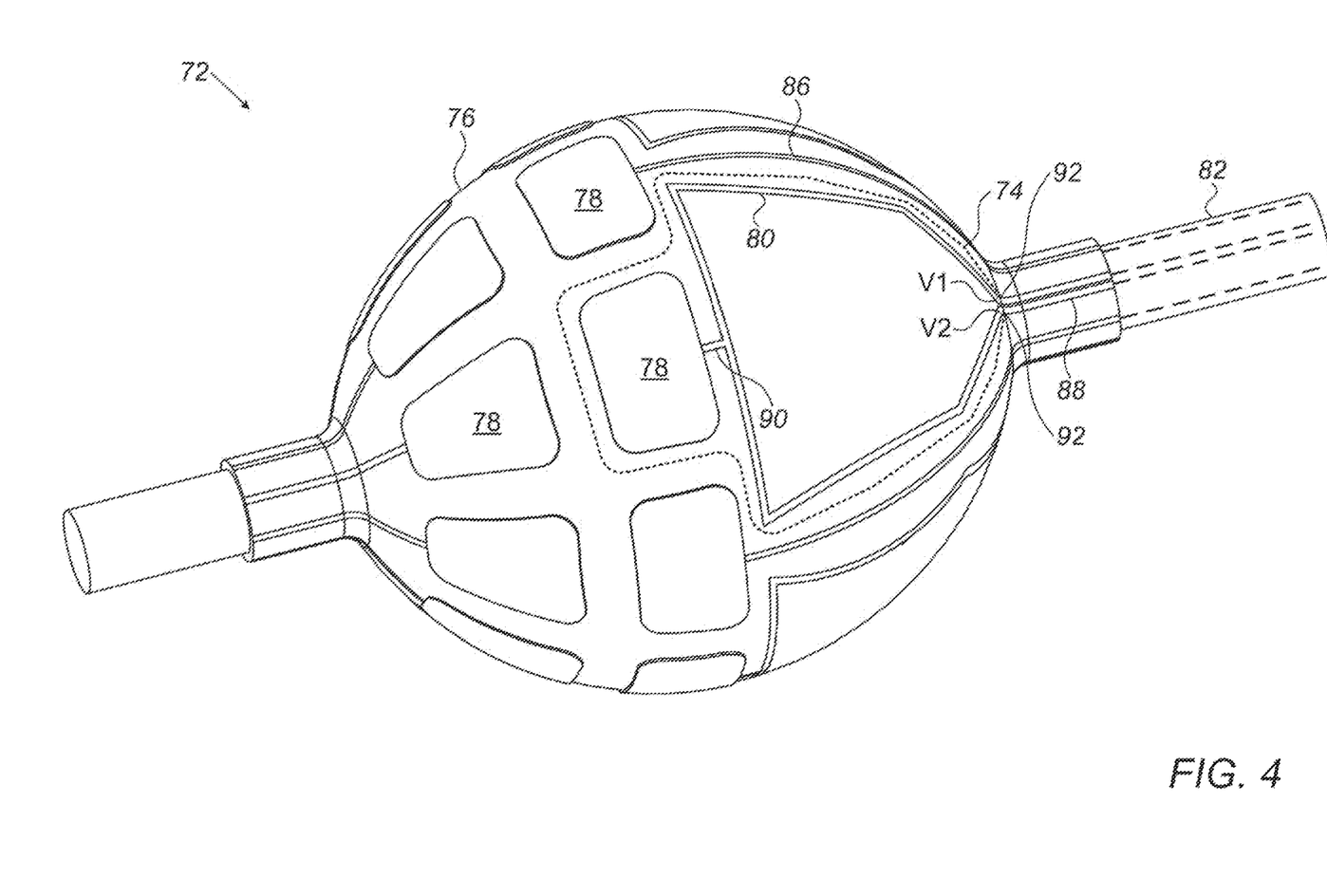
FIG. 4 is a schematic illustration of a catheter comprising multi-function conducting elements, in accordance with some embodiments of the present invention.

For example, reference is now made to FIG. 4, which is a schematic illustration of a catheter 72 comprising multi-function conducting elements 74, in accordance with some embodiments of the present invention. Catheter 72, which may be described as a "balloon catheter," comprises a balloon 76, located at or near the distal end of the shaft 82 of the catheter, and a plurality of multi-function conducting elements coupled to balloon 76. Conducting elements 74 may, for example, be printed onto the surface of the balloon, or may be coupled to the balloon in any other suitable way.

In some embodiments, each conducting element 74 comprises an electrode 78, configured to exchange signals with tissue, and a coil 80 electrically connected to electrode 78. As opposed to coils 80, which are generally electrically insulated from the tissue, electrodes 78 are not insulated, such that the electrodes may make electrical contact with the tissue. Leads (or "connections") 88, which run proximally-distally through shaft 82, connect the conducting elements to the proximal end of the catheter, which is connected to console 36 (FIG. 1). As shown in FIG. 4, catheter 72 may also comprise one or more additional electrodes 78, which are not coupled to coils, but instead, are coupled directly to leads 86.

Following the insertion of catheter 72 into the heart of a subject (as generally depicted in FIG. 1 for basket catheter 22), balloon 76 is inflated and one or more electrodes 78 are brought into contact with the intracardiac tissue. The electrodes then exchange signals with the tissue, e.g., by acquiring intracardiac ECG signals, and/or passing ablating signals into the tissue. Each such signal is carried to or from the relevant electrode by the coil and/or lead to which the electrode is attached. For example, in the case of an electrode belonging to a multi-function conducting element, each exchanged signal is carried between the conducting element and the proximal end of the catheter by a lead 88, and between the lead and the electrode by coil 80. (Coil 80 thus functions as a conductive trace.)

As shown in FIG. 4, leads 88 may be integrally formed with, and hence entirely continuous with, the coils, such that each coil may be described as the distal looped end of a single lead that runs distally through shaft 82, forms a loop along the surface of the balloon, and then returns, passing proximally, through the catheter shaft.

Coils 80 also output location-indicating signals in response to a magnetic field. In particular, in the presence of an externally-applied magnetic field, an alternating current (AC) voltage is induced in the coil, creating an AC voltage difference between the two terminals 92 of each coil, this voltage difference indicating the location and/or orientation of the coil relative to magnetic-field generators 30 (FIG. 1). For example, FIG. 4 shows an induced voltage difference V2–V1 between terminals 92 of one of the coils. This voltage difference is carried by leads 88 to the console. Processor 32 receives the voltage difference, and, in response to the voltage difference, ascertains the location and/or orientation of the coil (and hence, of the electrode to which the coil is connected).

(The "terminals" of the coil are the two points, at the proximal end of the coil, at which the coil becomes effectively closed, such that the coil meets, or "becomes," leads 88. At the proximal end of the coil, leads 88 may be in mechanical (but not electrical) contact with one another, and, in some embodiments, may cross over one another.)

The location-indicating signals from the conducting elements may be used to guide the conducting elements to the appropriate location(s) for signal exchange. For example, while a particular conducting element is in contact with tissue, a location-indicating signal may be received from the conducting element. If the location indicated by the location-indicating signal is a desired location for signal exchange, a signal may be exchanged with the tissue via the conducting element (and in particular, the electrode belonging to the conducting element) and at least one of its leads. Otherwise, the position and/or orientation of catheter 72 may be adjusted as appropriate, prior to the signal exchange.

Each coil may be situated proximally or distally to the electrode to which the coil is connected. Typically, as shown, the coil is flat, i.e., it is not a barrel coil, such that the coil does not overly protrude from the surface of the balloon. Typically, as shown, each coil is a single-loop coil. In some embodiments, as shown, the coil is shaped to define a polygon, e.g., a five-sided polygon. Alternatively, the coil may have any other suitable shape, such as that of a circle or ellipse. As shown, the coil may be connected to the electrode (e.g., at the "base" of the polygon) by a connecting wire 90.

In some embodiments, each coil 80 also functions as an electrode. For example, each coil may comprise, in addition to an insulated portion that is electrically insulated from the tissue, an uninsulated portion. This uninsulated portion, while in contact with the tissue, exchanges signals, such as ECG signals and ablation signals, with the tissue. The coil thus performs at least three functions: (i) the exchange of signals with the tissue, (ii) the carrying of these signals to or from the tissue, and (iii) the output of voltage differences in response to a magnetic field. It is noted that a conducting element 74 that comprises such a coil does not necessarily comprise an electrode 78 that is separate from the coil, since the coil may already perform the function of electrode 78.

In some embodiments, at least part of each of the conducting elements has an electrical resistance that varies in response to strain to which the conducting element is subjected inside the body of the subject. For example, coil 80, in whole or in part, may be made of a biocompatible strain-sensitive material, and/or may have a form that renders the coil sensitive to strain. In such embodiments, the strain exerted on each of the conducting elements may be measured, by measuring the electrical resistance of the conducting elements. For example, a current of known amplitude (and a frequency different from that of the generated magnetic field) may be passed through each of the conducting elements via the leads connected thereto, and the resulting voltage between the proximal terminals of the leads may be measured. This voltage, divided by the amplitude of the current (and taking into account the electrical resistance of the leads), gives the electrical resistance of the conducting element, which in turn indicates the magnitude of the strain applied to the conducting element. The strain applied to the catheter may then be derived from the strains that were measured for the conducting elements.

Alternatively or additionally, each of the conducting elements may comprise a thermocouple junction. In other words, each of the conducting elements may comprise two portions, made of different metals, connected to one another at a temperature-sensing junction, such that each of the conducting elements functions as a thermocouple temperature sensor. For example, a portion of coil 80 may be made of copper, and another portion of the coil may be made of constantan, the copper and constantan being connected to one another at a thermocouple junction. Such a junction may be located, for example, at the distal end of coil 80, e.g., at the point at which coil 80 meets connecting wire 90.

Alternatively, such a junction may be located anywhere else along coil 80, or along one of leads 88. In such embodiments, a thermocouple junction may be used to measure the temperature of the tissue and/or of the ambient environment. For example, while a thermocouple junction is contacting the subject's tissue, the temperature of the tissue may be measured, by measuring the voltage difference across the leads. (This voltage is a direct current (DC) voltage, such that it may be differentiated from the alternating voltage induced by the generated magnetic field.)

Alternatively or additionally, an electric current may be passed between the conducting element and a patch coupled to skin of the subject, such as to measure the impedance between the conducting element and the patch. Such an impedance measurement may be used, for example, for an impedance-based tracking system, whereby the location of the conducting element is ascertained in response to the measured impedance, alternatively or additionally to being ascertained in response to the voltage induced in the conducting element by a generated magnetic field.

It is noted that the above-described strain, temperature, and impedance measurements may also be performed by conducting elements 24, described above with respect to FIG. 1, as well as by any other suitable multi-function conducting elements. The multi-function conducting elements described herein may be coupled to an expandable structure, such as basket 20 of FIG. 1 or balloon 76 of FIG. 4, or to any other suitable tool.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) an expandable structure extending along a longitudinal axis, configured for insertion into a body of a subject; and
   (b) a plurality of conducting elements disposed on a surface of the expandable structure, each of the plurality of conducting elements comprising a respective coil having two terminals, each of the coils is configured to induce an alternating current (AC) voltage difference between the two terminals in response to an external magnetic field, each of the coils including:
   i) an insulated portion of the coil electrically insulated from tissue of the subject, and
   ii) an uninsulated portion of the coil connected electrically to the two terminals, the uninsulated portion configured to exchange signals with the tissue of the subject while in contact with the tissue of the subject.

2. The apparatus according to claim 1, wherein the uninsulated portion comprises an electrode to pass ablating signals into the tissue.

3. The apparatus according to claim 1, wherein the uninsulated portion comprises an electrode to acquire ECG signals from the tissue.

4. The apparatus of claim 1, wherein the expandable structure comprises a balloon.

5. The apparatus according to claim 1, wherein the expandable structure comprises a basket, the basket includes a plurality of splines configured to expand into a generally spheroidal structure such that each spline defines a portion of the surface of the expandable structure.

6. The apparatus according to claim 1, further comprising a separate electrode connected to the coil, the electrode being configured to exchange the signals with the tissue, and the coil being configured to carry the exchanged signals from the electrode.

7. The apparatus according to claim 6, wherein the coil is situated proximally to the conducting elements to which the coil is connected.

8. The apparatus according to claim 1, wherein the coil comprises a single-loop coil.

9. The apparatus according to claim 1, wherein the coil comprises a helical coil.

10. The apparatus according to claim 1, wherein the coil comprises a generally flat coil disposed on a generally spherical surface of the expandable structure.

11. A system, comprising:
    (a) an expandable structure, configured for insertion into a body of a subject; and
    (b) a plurality of conducting elements disposed on a surface of the expandable structure, each of the plurality of conducting elements comprising a respective coil having two terminals, each of the coils is configured to induce an alternating current (AC) voltage difference between the two terminals in response to an external magnetic field, each of the coils having:
    i) an insulated portion of the coil electrically insulated from tissue of the subject, and
    ii) an uninsulated portion of the coil connected electrically to the two terminals, the uninsulated portion configured to exchange signals with the tissue of the subject while in contact with the tissue of the subject; and
    (c) a processor, the processor configured to:
    i) receive the exchanged signals from the uninsulated portion; and
    ii) receive an output of the AC voltage difference between the two terminals in response to the external magnetic field.

12. The system according to claim 11, wherein at least part of each conducting element of the conducting elements has an electrical resistance that varies in response to strain to which the conducting element is subjected inside the body of the subject.

13. The system according to claim 11, wherein each of the conducting elements comprises a thermocouple junction.

14. The system according to claim 11, wherein the processor is configured to measure a second voltage difference representative of temperature across the two terminals.

15. The system of claim 11, wherein the processor is configured to measure an impedance between each of the conducting elements and a patch coupled to skin of the subject via an electric current provided between the conducting elements and the patch.

* * * * *